United States Patent

Hubbard et al.

[11] Patent Number: 4,798,199
[45] Date of Patent: Jan. 17, 1989

[54] ARTERIAL WRIST SUPPORT

[75] Inventors: Vance M. Hubbard; Welton K. Brunson, both of Bedford, Tex.

[73] Assignee: Tecnol, Inc., Fort Worth, Tex.

[21] Appl. No.: 821,225

[22] Filed: Jan. 21, 1986

Related U.S. Application Data

[63] Continuation of Ser. No. 579,774, Feb. 13, 1984, abandoned.

[51] Int. Cl.⁴ ............................................. A61F 5/04
[52] U.S. Cl. ................................. 128/87 R; 128/89 R; 128/845
[58] Field of Search ............... 128/DIG. 6, 133, 87 R, 128/88, 89 R

[56] References Cited

U.S. PATENT DOCUMENTS

| | | | |
|---|---|---|---|
| 2,266,231 | 12/1941 | Mazzeo et al. | 128/DIG. 6 X |
| 3,256,880 | 6/1966 | Caypinar | 128/133 |
| 3,640,273 | 2/1972 | Ray | 128/87 |

FOREIGN PATENT DOCUMENTS 2601739  7/1976  Fed. Rep. of Germany ... 128/132 R

Primary Examiner—William R. Dixon, Jr.
Assistant Examiner—Karl Group
Attorney, Agent, or Firm—Jerry W. Mills; Jefferson Perkins

[57]  ABSTRACT

An arterial wrist support for supporting a patient's extremity for arterial or intravenous care includes a substantial rigid, unitary molded body (12) adapted to matingly engage the patient's hand, wrist and at least a portion of the patient's forearm. Body (12) is anatomically shaped to accommodate the contours of the patient's arm and to position the patient's wrist at the proper angle to expose the radial artery for accurate, efficient handling of the arterial puncture. A removable pad (34) dimensioned to be positioned beneath the patient's wrist is provided and may be used to increase the angle of orientation of the patient's wrist to receive and start the arterial line. Wide resilient straps (20, 22) hold the patient's arm in position on body (12). Releasable contact fastening members (24) are fixed along the underside of body (12) for securing straps (20, 22) thereto.

13 Claims, 2 Drawing Sheets

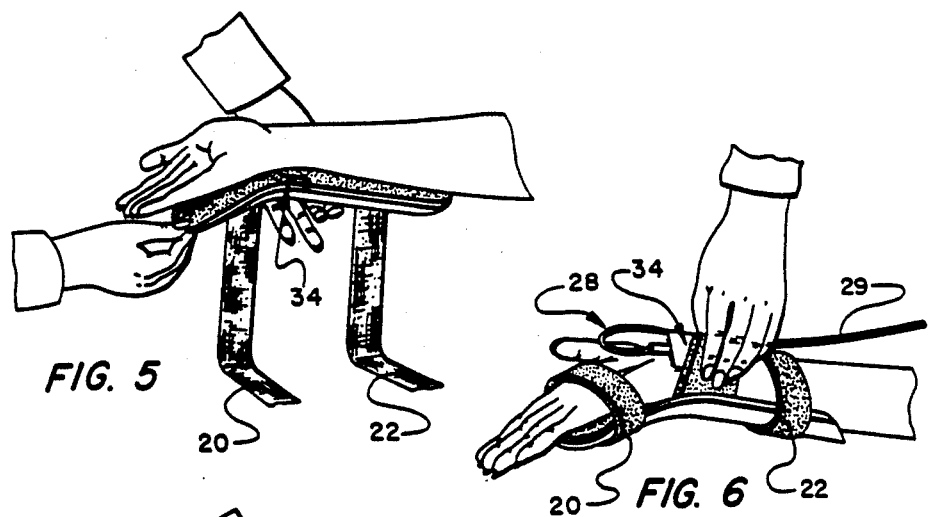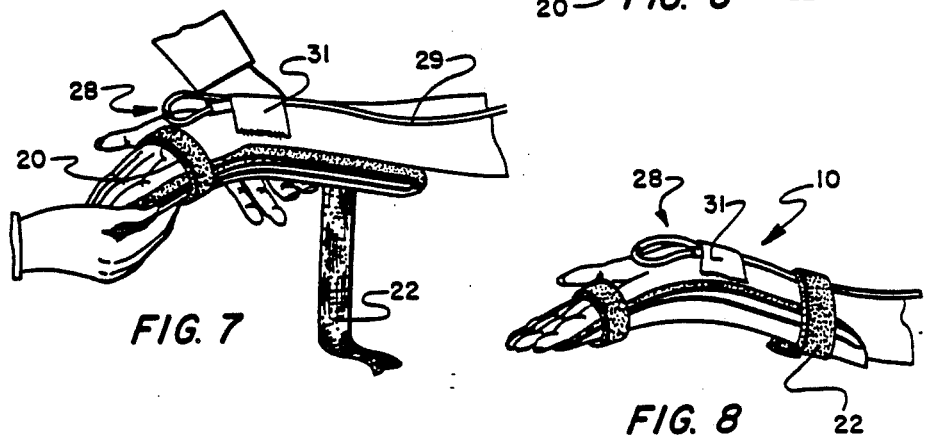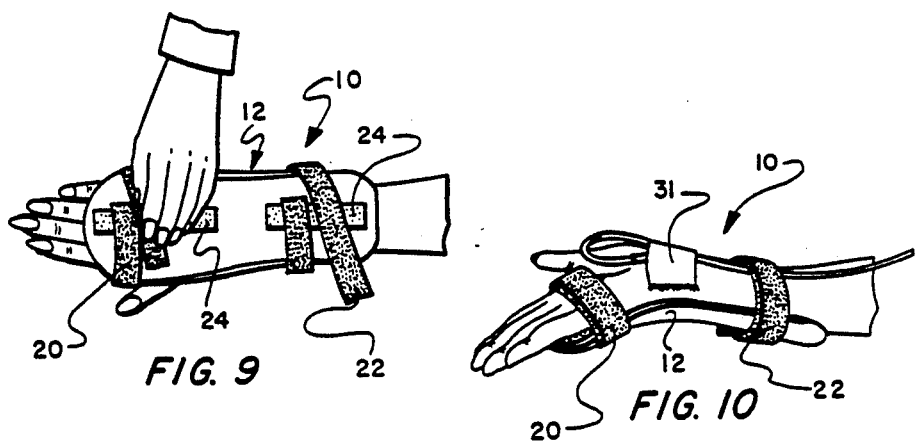

4,798,199

ARTERIAL WRIST SUPPORT

This application is a continuation of application Ser. No. 579,774, filed Feb. 13, 1984, now abandoned.

TECHNICAL FIELD

This invention relates to arm supporting devices generally and more specifically to a device for supporting and positioning a patient's hand, wrist, and a portion of the forearm for administering arterial or intravenous therapy.

BACKGROUND OF THE INVENTION

Individuals undergoing medical care in a hospital environment commonly require arterial therapy (e.g., invasive monitoring of blood gases) or the infusion of intravenous fluids, particularly during and after surgery. It is important in such therapy that the patient's wrist be properly oriented in an angled position to easily receive and start the arterial or intravenous line. A continuing need thus exists for an economic, convenient and effective apparatus for supporting a patient's wrist and forearm for such therapy.

Traditionally, arterial and intravenous lines have been administered by supporting the patient's arm on an improvised armboard formed by a flat piece of rigid cardboard or wood and securing the patient's arm thereto with strips of adhesive tape. Towels or other padding materials have been positioned beneath the patient's wrist to properly angle the wrist to receive and start the arterial or intravenous line. The padding materials are removed once the line has been started. Such prior techniques are tedious and utilize the time of valuable hospital personnel who would otherwise be free to perform other duties. In addition, the materials used in constructing such armboards are not always readily available and are relatively costly.

The traditional armboards, moreover, often do not properly position the patient's wrist to receive the line and are uncomfortable for the patient. Because prior armboards have not normally been shaped to accommodate the contours of the patient's arm, a relatively hard surface is presented which does not conform to the shape of the patient's arm. Adhesive tape is thus required to stabilize the arm, such tape tending to abrade hair and skin in the contact areas and frequently causing adverse skin reactions.

It is also not uncommon with the traditional technique for a patient to accidentally disconnect the arterial or intravenous line by flexing his wrist, or for a nurse or other medical professional to require substantial time to start the arterial or intravenous line. Aside from the costly nature of such start-up time and required restarts, the time for starting and restarting the line may be detrimental to the patient's welfare.

The present invention obviates the disadvantages associated with the traditional armboards by providing a preformed unitary support which can be readily and inexpensively manufactured by a simple molding process. Wide resilient foam straps replace costly and skin damaging adhesive tape to secure the patient's arm to the support. The straps effectively immobilize the patient's wrist and thus prevent wrist flexing. The support is anatomically shaped to fit the contours of the patient's arm and to position the patient's wrist at the proper angle for accurate and efficient handling of the arterial or venous puncture. The support also includes a removable flexible pad dimensioned to be optionally positioned beneath the patient's wrist to thus increase the angle of orientation of the wrist for receiving and starting the arterial or intravenous line. Once the line is started, the pad is removed. Because the support is contoured to fit the shape of the human arm, the patient's arm is supported in a comfortable and relaxed position.

SUMMARY OF THE INVENTION

The present invention described and disclosed herein comprises an arterial wrist support for invasive monitoring of a patient's blood gases during and after surgery. The apparatus is designed to support a patient's hand, wrist, and at least a portion of the patient's forearm in a relaxed position which allows for efficient starting of the arterial line and continuous maintenance, observation and cleaning of the arterial site. The apparatus may also be effectively used in the administration of intravenous care.

More specifically, the arterial wrist support of the present invention includes a substantially rigid, lightweight, unitary molded body anatomically shaped to accommodate the contours of a patient's arm and to position the patient's wrist at the proper angle to expose the radial artery for accurate and efficient handling of the arterial puncture. The support also includes a removable foam pad which may be positioned beneath the patient's wrist to increase the angle of orientation of the wrist for receiving and starting the arterial line and removed once the line is started. Wide resilient straps adapted to be releasably secured to the molded body are provided to attach the body to the patient's arm and thus immobilize the patient's wrist. The molded body also includes a foam pad lining located on its upper surface and extending along its length to cushion the patient's hand and wrist and thus provide a soft comfortable support.

Replacing costly improvised methods, the preformed support apparatus of the present invention simplifies set-up procedures and provides greater patient comfort and hospital cost containment. Because the apparatus totally supports the patient's hand and wrist, the nurse's, or other medical professional's, hands are free to start the arterial or intravenous line. Costly materials, e.g., adhesive tape, are eliminated and accurate, efficient handling results in fewer expensive restarts.

BRIEF DESCRIPTION OF DRAWINGS

A more complete understanding of the invention can be had by reference to the following detailed description taken in conjunction with the accompanying Drawing in which:

FIG. 5 is a perspective view of the arterial wrist support of FIG. 1 illustrating the positioning of the patient's wrist on the device with the flexible pad positioned beneath the wrist;

FIG. 6 is a perspective view of the arterial wrist support of FIG. 1 illustrating the removal of the pad in FIG. 5 after the arterial line has been started;

FIG. 7 is a perspective view of the arterial wrist support of FIG. 1 illustrating the positioning of the patient's wrist on the device;

FIG. 8 is a perspective view of the arterial wrist support of FIG. 1 illustrating the placement of straps to hold the patient's arm in position on the device;

FIG. 9 is a bottom view of the arterial wrist support of FIG. 1; and

FIG. 10 is a perspective view of the arterial wrist support of FIG. 1 when in use.

DETAILED DESCRIPTION OF INVENTION

Figure 1:
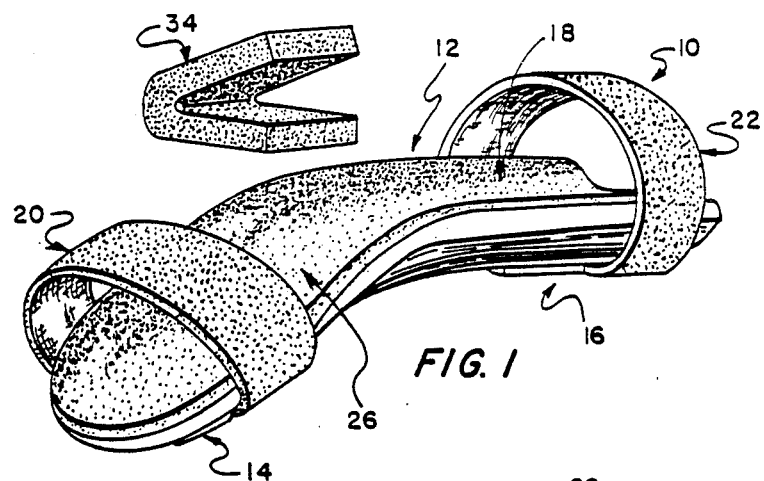
FIG. 1 is a perspective view of an arterial wrist support constructed in accordance with the present invention.

Referring now to the Drawing, wherein like reference numerals designate like or corresponding parts throughout the views, FIG. 1 shows a perspective representation of the arterial wrist support of the present invention. The support 10 includes a substantiall rigid molded body 12 adapted to matingly engage the back of the patient's hand, wrist and at least a portion of the patient's forearm to support the patient's arm in a substantially relaxed position for arterial care.

Figure 2:
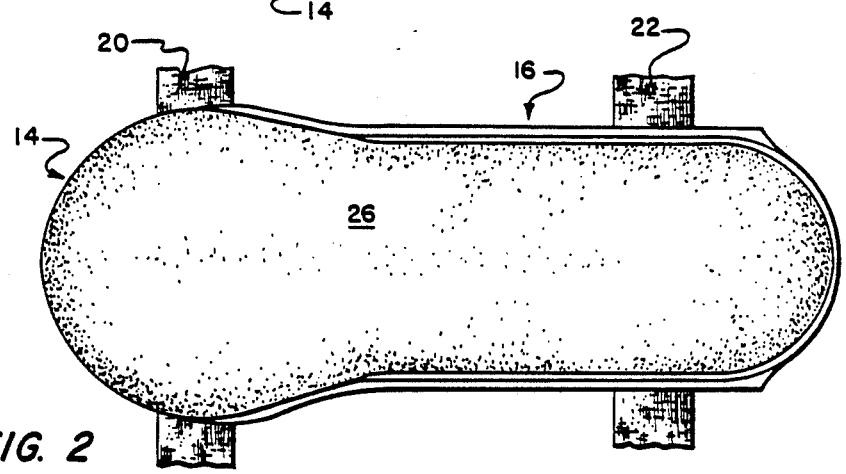
FIG. 2 is a top view of the arterial wrist support of FIG. 1.
Figure 3:
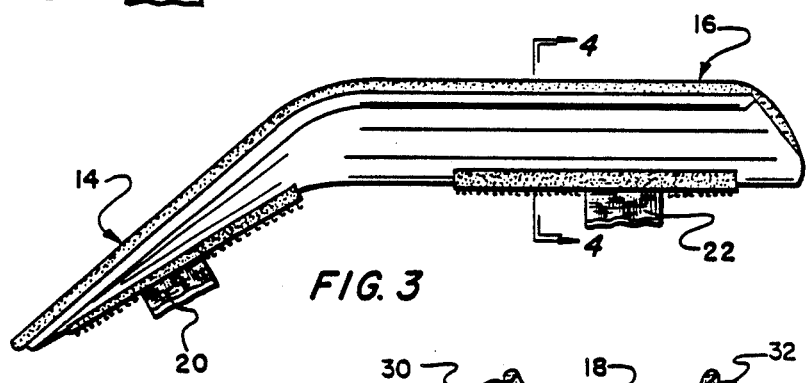
FIG. 3 is a side view of the arterial wrist support of FIG. 1.
Figure 4:
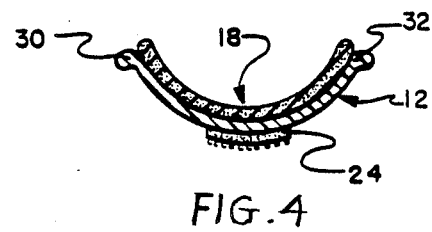
FIG. 4 is a sectional view taken along lines 4—4 of FIG. 3 in the direction of the arrows.

Body 12 includes a forward portion 14 for receiving the back of the patient's hand and a rear portion 16 integrally connected thereto for receiving the patient's wrist and forearm. Forward portion 14 is spoon-shaped, as shown in FIG. 2, is substantially concave at the upper surface as shown in FIG. 1, and slopes downwardly from rear portion 16, as shown in FIG. 3. Rear portion 16 is substantially concave and is disposed relative to forward portion 14 to support the patient's wrist at the proper angle to expose the radial artery for receiving the arterial puncture. As shown in FIGS. 1 and 4, a transversely arcuate channel 18 is defined which extends along rear portion 16 to the trailing edge of molded body 12 to define a cradle to receive the back of the patient's forearm. Rolled or turned edge channels 30 and 32 (FIG. 4) extend along the length of body 12 to rigidify the body. In the preferred embodiment, when the evice is used for adults, body 12 is approximately 9½ inches long, forward portion 14 is approximately 4 inches long and sloped downwardly from rear portion 16 at an approximate angle of 30 degrees, and rear portion 16 is approximately 5½ inches long.

Body 12 may be formed of any suitable rigid material which may be formed in the desired shape. In the preferred embodiment, body 12 is formed of lightweight semi-rigid plastic, injection molded to the contoured configuration described above.

Referring to FIGS. 1-4, support 10 also includes wide resilient straps 20 and 22 for holding the patient's arm in position on body 12. At least the inside surfaces of straps 20 and 22 are contact fastening surfaces and may be of various resilient contact fastening materials, e.g., pile fabric. Releasable contact fastening members 24 (FIG. 9) are affixed along the underside of body 12 for securing straps 20 and 22 thereto. Contact fastening members 24 may be of various materials, for example, material sold under the trademark "VELCRO", which grips the pile fabric of straps 20 and 22. A pad 26 made of foam rubber or other suitable absorbent material is provided on the skin contacting upper surface of body 12 and along its length to cushion the patient's arm and thus offer the patient a soft, comfortable support. A removable pad 34 made of foam rubber or other suitable material and dimensioned to be bent double and positioned beneath the patient's wrist is used to increase the angle of orientation of the wrist for receiving the arterial line. In the preferred embodiment, Pad 34 has a length of 5 inches, a width of 1¾ inches and a thickness of ½ inch. Pad 34 is removed once the line is started.

FIG. 5 illustrates the initial positioning of the patient's wrist on support 10 with pad 34 being positioned therebeneath to start the arterial line. Straps 20 and 22 are then firmly wrapped around the patient's arm and affixed under support 10 to control fastening members 24. In FIG. 6, pad 34 is removed after a needle 28 carrying the line has been inserted into the patient's wrist. It will be noted in this position that the tube 29 leading from needle 28 is not affixed under strap 22.

As depicted in FIG. 7, strap 22 is thus removed at one end from support 10 and rewrapped over tube 29 as shown in FIG. 8. Adhesive 31 may be used to firmly hold needle 28 in place.

FIG. 9 illustrates how straps 20 and 22 are releasably secured to body 12 by pressing the straps against the contact fastening members 24 located on the underside of body 12. Straps 20 and 22 may be removed and relocated as desired. FIG. 10 illustrates how the patient's wrist is immobilized and the arterial line held in the desired position by the present support.

In summary, an arterial wrist support has been disclosed to support a patient's arm in a comfortable and relaxed position for arterial therapy. The support is contoured to fit the shape of the patient's arm, and anatomically shaped to position the patient's wrist at the proper angle to expose the radial artery for accurate, efficient handling of the arterial puncture. A removable foam pad is provided to be positioned beneath the patient's wrist to increase the angle of orientation of the wrist for receiving and starting the arterial line. Wide resilient straps secure the wrist comfortably so that the arterial line can be started and maintained, eliminating possible wrist flexing and the need for restarts. A pad lining cushions the hand and wrist to offer the patient a soft, comfortable support. The support may also be effectively used in the administration of intravenous care.

Although the preferred embodiment has been described in detail, it should be understood that various changes, substitution and alterations can be made therein without departing from the spirit and scope of the invention as defined by the appended claims.

We claim:

1. Apparatus for supporting a patient's hand, wrist, and at least a portion of the forearm in order to expose the radial artery to receive an arterial line, comprising:
a substantially rigid, unitary body adapted to underlie the posterior of the patient's hand, wrist and forearm, said body including:
   a substantially concave, spoon-shaped forward portion for mating engagement with the posterior surface of the hand, between the wrist and the distal ends of the fingers, said concave shape extending upwards around the medial and lateral sides of the hand towards the anterior side thereof to prevent rotation of the hand about the wrist joint, and
   a substantially concave forearm support portion being integrally connected to the end of said forward portion proximate the wrist for receiving the patient's forearm,
   said forearm portion having a traversely arcuate channel formed therein and extending along said forearm portion from said forward portion at the wrist towards the elbow for receiving the portion of the patient's forearm cooperating with the wrist, the transverse shape of said forearm portion being concave for preventing rotation of the forearm about the wrist, said forward portion and said forearm portion being of unitary construction, said forward portion being oriented at an angle relative to said rear portion so that the patient's wrist is supported at an obtuse angle such that the hand is rotated about the wrist away from the anterior side to expose the radial artery to receive an arterial puncture; and releasable fastening means for attaching said body to the hand and forearm to provide immobilizing support to the wrist and the arterial line, said fastening means comprising means for securing the palm of the hand below the thumb to said forward portion and means securing the forearm substantially above the wrist to said forearm support portion, a wrist region between said means for securing the palm and said means for securing the forearm remaining free for the insertion of said arterial line thereat.

2. The apparatus of claim 1 wherein said fastening means comprises contact engaging means for both the hand and the forearm, said engaging means having first and second engaging portions, the first portion being fixedly secured to the underside of said body and the second portion including at least one strap having first and second ends for being secured to said first portion, said strap being attached to said body by wrapping said strap around the respective hand or forearm and securing said first and second ends to said first portion, said first portion allowing said second portion to be disposed an adjustable distance from the wrist.

3. The apparatus of claim 1 further comprising a pad lining affixed to the upper surface of said body and extending along the length of said body to cushion the patient's hand, wrist and forearm.

4. The apparatus of claim 3 wherein said pad lining comprises foam rubber material.

5. The apparatus of claim 1 and further comprising a removable pad dimensioned to be removably positioned on the upper surface of said body beneath the patient's wrist to decrease said obtuse angle to further rotate the hand about the wrist away from the anterior side thereof to receive an arterial puncture.

6. The apparatus of claim 5 wherein said removable pad comprises resilient foam rubber material.

7. The apparatus of claim 1 wherein said body includes edge channels turned to further rigidify the body.

8. A device for supporting a patient's hand, wrist and the portion of the forearm proximate the wrist to receive an arterial line in the arteries proximate the wrist, comprising:

means for supporting the hand disposed on the posterior side of the hand;

means for supporting the patient's forearm and for being disposed on the posterior side thereof;

means for interconnecting said hand support means and said forearm support means at an obtuse angle proximate the wrist joint such that the hand is rotated about the wrist away from the anterior side thereof such that access to the arteries associated with the anterior side of the wrist are made more accessible to a medical technician requiring access thereto;

means for immobilizing the hand to prevent rotation about the wrist, said means applied to the hand below the thumb; and means for immobilizing the forearm substantially above the wrist to prevent rotation about the wrist joint, said means for immobilizing the hand and said means for immobilizing the forearm leaving the wrist free for receiving said arterial line thereat.

9. The apparatus of claim 8 and further comprising removable means for temporarily decreasing the obtuse angle that the hand makes with the forearm such that the hand is further rotated about the wrist away from the anterior side thereof to further increase access to the arteries in the wrist, said removable means removable after the arterial line is inserted.

10. A method for supporting a patient's hand, wrist and forearm for receiving an arterial line, comprising:

supporting the posterior side of the hand with a first rigid member with respect to the wrist joint to prevent rotation thereof about the wrist joint;

supporting the forearm proximate the wrist joint with a second rigid platform, the rigid platform being shaped to prevent rotation of the forearm about the wrist joint when the forearm is disposed thereon; and maintaining an obtuse angle between the first rigid platform and the second rigid platform such that the hand is rotated about the wrist away from the anterior side thereof to allow access to the arteries of the wrist for insertion of an arterial line, the obtuse angle maintained while the arterial line is in place;

securing the hand on the first rigid platform below the thumb to prevent rotation thereof about the wrist; and securing the forearm to the second rigid platform substantially above the wrist to prevent rotation thereof about the wrist joint with respect to the hand.

11. The method of claim 10 wherein the step of securing the hand and the wrist comprises:

disposing a strap having first and second free ends about the anterior surface of the forearm with the free ends thereof contacting the underside of the second rigid platform;

removably securing the free ends of the forearm strap on the underside of the second rigid platform;

disposing a strap having a first and second free ends about the anterior surface of the hand and extending around to the underside of the first rigid platform such that the free ends contact the underside thereof; and removably securing the free ends of the hand strap to the underside of the first rigid platform;

the hand strap and wrist strap removably secured to the undersides of the first and second rigid platforms, respectively, such that the distance between the respective straps and the wrist is adjustable.

12. The method of claim 10 and further comprising:

temporarily decreasing the obtuse angle and rotating the hand about the wrist away from the anterior side thereof to increase access to the arteries in the wrist for insertion of the arterial line, the angle returned to the normal obtuse angle after insertion of the catheter line.

13. The method of claim 12 wherein the forearm support and the hand support form a continual surface underneath the wrist wherein the step of temporarily decreasing the obtuse angle comprises inserting a pad between the portion of the forearm support proximate the wrist to decrease the obtuse angle, the pad being removed after insertion of the arterial line.

* * * * *